US012023264B2

(12) United States Patent
Lee et al.

(10) Patent No.: US 12,023,264 B2
(45) Date of Patent: Jul. 2, 2024

(54) ACTUATOR AND MOTION ASSISTANCE APPARATUS INCLUDING THE SAME

(71) Applicant: Samsung Electronics Co., Ltd., Suwon-si (KR)

(72) Inventors: Jongwon Lee, Suwon-si (KR); Youngjin Park, Seoul (KR); Youn Baek Lee, Yongin-si (KR); Jeonghun Kim, Suwon-si (KR); Se-Gon Roh, Suwon-si (KR); Minhyung Lee, Seoul (KR); Byungjune Choi, Gunpo-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 355 days.

(21) Appl. No.: 17/308,512

(22) Filed: May 5, 2021

(65) Prior Publication Data

US 2021/0251780 A1 Aug. 19, 2021

Related U.S. Application Data

(63) Continuation of application No. 15/912,818, filed on Mar. 6, 2018, now Pat. No. 11,020,249.

(30) Foreign Application Priority Data

Oct. 16, 2017 (KR) .......................... 10-2017-0133966

(51) Int. Cl.
*A61H 3/00* (2006.01)
*A61B 5/107* (2006.01)
(Continued)

(52) U.S. Cl.
CPC .............. *A61F 2/68* (2013.01); *A61B 5/1071* (2013.01); *A61H 1/0237* (2013.01);
(Continued)

(58) Field of Classification Search
CPC ........................................................ A61H 3/00
See application file for complete search history.

(56) References Cited

U.S. PATENT DOCUMENTS 5,213,544 A 5/1993 Wolf et al.
6,119,840 A 9/2000 Dettmar
(Continued)

FOREIGN PATENT DOCUMENTS

CN 87104205 A 1/1988
CN 2301575 Y 12/1998
(Continued)

OTHER PUBLICATIONS

Extended European Search Report dated Mar. 13, 2019, issued in corresponding European Patent Application No. 18188300.0.
(Continued)

*Primary Examiner* — Jacqueline Wozznicki
(74) *Attorney, Agent, or Firm* — Harness, Dickey & Pierce, P.L.C.

(57) ABSTRACT

An actuator includes a plurality of power transmitters configured to transmit power sequentially, and an elastic element configured to connect a first power transmitter and a second power transmitter that are adjacent to each other and perform a coaxial rotation motion, among the plurality of power transmitters.

19 Claims, 13 Drawing Sheets

(51) Int. Cl.
*A61F 2/68* (2006.01)
*A61H 1/02* (2006.01)
*A61F 2/74* (2006.01)
*A61F 2/76* (2006.01)
*A61F 5/01* (2006.01)

(52) U.S. Cl.
CPC ......... *A61H 1/0244* (2013.01); *A61H 1/0274* (2013.01); *A61H 3/00* (2013.01); *A61F 2/741* (2021.08); *A61F 2002/7625* (2013.01); *A61F 2002/7635* (2013.01); *A61F 2002/7645* (2013.01); *A61F 5/0111* (2013.01); *A61H 2003/007* (2013.01); *A61H 2201/1215* (2013.01); *A61H 2201/14* (2013.01); *A61H 2201/1472* (2013.01); *A61H 2201/1628* (2013.01); *A61H 2201/164* (2013.01); *A61H 2201/165* (2013.01); *A61H 2201/1676* (2013.01); *A61H 2201/5007* (2013.01)

(56) References Cited

U.S. PATENT DOCUMENTS

| | | | |
|---|---|---|---|
| 6,342,012 | B1 | 1/2002 | Dorok et al. |
| 8,075,633 | B2 | 12/2011 | Herr et al. |
| 8,435,309 | B2 | 5/2013 | Gilbert et al. |
| 2009/0299480 | A1 | 12/2009 | Gilbert et al. |
| 2010/0298746 | A1* | 11/2010 | Shimizu ................ B25J 9/0006 601/35 |
| 2014/0088729 | A1 | 3/2014 | Herr et al. |
| 2014/0114439 | A1 | 4/2014 | Iversen et al. |
| 2014/0142474 | A1 | 5/2014 | McBean et al. |
| 2016/0038368 | A1 | 2/2016 | Lee et al. |
| 2016/0106615 | A1* | 4/2016 | Lee ........................ A61H 3/00 414/4 |
| 2016/0235578 | A1* | 8/2016 | Romo .................. A61F 5/0127 |
| 2017/0027735 | A1 | 2/2017 | Walsh et al. |
| 2017/0165088 | A1 | 6/2017 | Lefeber et al. |
| 2020/0121478 | A1 | 4/2020 | Woge et al. |
| 2021/0085551 | A1* | 3/2021 | Gregg ...................... A61F 2/70 |

FOREIGN PATENT DOCUMENTS

| | | | | |
|---|---|---|---|---|
| CN | 1372623 | A | 10/2002 | |
| CN | 1387616 | A | 12/2002 | |
| CN | 1447039 | A | 10/2003 | |
| CN | 103373343 | A | 10/2013 | |
| CN | 106361474 | A | 2/2017 | |
| DE | 3621187 | A1 | 1/1988 | |
| DE | 102014217809 | A1 | 3/2016 | |
| EP | 2 178 680 | B1 | 5/2014 | |
| EP | 2982360 | A2 * | 2/2016 | ............. A61H 1/024 |
| FR | 2809355 | A1 | 11/2001 | |
| JP | 2006-002805 | A | 1/2006 | |
| KR | 10-2016-0017953 | A | 2/2016 | |
| KR | 1020160098354 | A | 8/2016 | |
| WO | WO-2010/120404 | A2 | 10/2010 | |
| WO | WO-2015/029345 | A1 | 3/2015 | |

OTHER PUBLICATIONS

Notice of Preliminary Rejection dated Dec. 21, 2021 in Korean Application No. 10-2017-0133966.
Second Office Action dated May 26, 2023 in Chinese Application No. 201810801115.9.
The First Office Action dated Dec. 28, 2022 for the corresponding Chinese Application No. 201810801115.9.

* cited by examiner

ACTUATOR AND MOTION ASSISTANCE APPARATUS INCLUDING THE SAME

CROSS-REFERENCE TO RELATED APPLICATION

This application is a continuation application of U.S. application Ser. No. 15/912,818, filed on Mar. 6, 2018, which claims under 35 U.S.C. § 119 to Korean Patent Application No. 10-2017-0133966, filed on Oct. 16, 2017, in the Korean Intellectual Property Office, the entire contents of each of which are incorporated herein by reference in their entirety.

BACKGROUND

1. Field

At least one example embodiment relates to an actuator and/or a motion assistance apparatus including the same.

2. Description of the Related Art

An actuator is a driving apparatus that operates a machine using power, and may be used to drive various apparatuses such as a robots and an industrial facility. For example, the actuator may drive joint portions of a motion assistance apparatus that enables the elderly and/or patients having joint problems to walk with less effort.

SUMMARY

Some example embodiments relate to an actuator.

In some example embodiments, the actuator includes a plurality of power transmitters configured to transmit power sequentially, the plurality of power transmitters including a first power transmitter and a second power transmitter, the first power transmitter and the second power transmitter being adjacent ones of the plurality of power transmitters and configured to perform coaxial rotation motion; and an elastic element configured to connect the first power transmitter and the second power transmitter.

In some example embodiments, the actuator further includes a first angle sensor configured to measure a first rotation angle of the first power transmitter; a second angle sensor configured to measure a second rotation angle of the second power transmitter; and a controller configured to determine a torque to apply between the first power transmitter and the second power transmitter based on the first rotation angle and the second rotation angle.

In some example embodiments, the controller is configured to determine the torque based on a difference between the first rotation angle and the second rotation angle.

In some example embodiments, the actuator further includes a motor configured to transmit the power to the plurality of power transmitters; and a case including a motor receiver and a main receiver such that the motor receiver overlaps at least a portion of the main receiver in a direction perpendicular to a drive shaft of the motor, the motor receiver configured to receive the motor, and the main receiver configured to receive the first power transmitter, the second power transmitter, and the elastic element.

In some example embodiments, the case further includes a cover detachably coupled to one side of each of the motor receiver and the main receiver.

In some example embodiments, the first power transmitter is ring-shaped, and the elastic element is between an inner wall of the first power transmitter and an outer wall of the second power transmitter.

In some example embodiments, the first power transmitter, the elastic element, and the second power transmitter are an integral body.

In some example embodiments, the elastic element includes a body; a first connector with a first end fixed to the inner wall of the first power transmitter and a second end fixed to a portion of the body adjacent to the outer wall of the second power transmitter; and a second connector with a first end fixed to the outer wall of the second power transmitter and a second end fixed to a portion of the body adjacent to the inner wall of the first power transmitter.

In some example embodiments, the body has a circular shape, the first connector has a curved shape that encloses a first portion of the body, and the second connector has a curved shape that encloses a second portion of the body.

In some example embodiments, the elastic element includes a plurality of elastic elements spaced apart from each other at equal intervals about a rotation axis shared by the first power transmitter and the second power transmitter.

In some example embodiments, two adjacent elastic elements of the plurality of elastic elements are in contact with each other when the first power transmitter and the second power transmitter rotate relative to one another by a set angle.

In some example embodiments, the plurality of power transmitters comprise: a first planetary gear having a rotation axis rotatably fixed to the first power transmitter, the first planetary gear configured to revolve around a rotation axis of the first power transmitter; a first sun gear configured to transmit the power to the first planetary gear; a second planetary gear configured to engage with an outer circumferential surface of the second power transmitter, and revolve around a rotation axis of the second power transmitter; a carrier to which the second planetary gear is rotatably installed, the carrier configured to perform the coaxial rotation motion with the second power transmitter; and a ring gear configured to engage with the first planetary gear and the second planetary gear.

In some example embodiments, the actuator further includes a motor configured to generate the power to drive the plurality of power transmitters, wherein the plurality of power transmitters further include a gear train configured to connect the motor and the first sun gear.

In some example embodiments, the gear train has a first side and a second side, and the motor, the first power transmitter, the second power transmitter, and the elastic element are on a same one of the first side and the second side of the gear train.

In some example embodiments, the actuator includes at least one stopper configured to change a gear ratio between the first sun gear and the carrier by selectively fixing one of the first power transmitter and the ring gear.

In some example embodiments, the at least one stopper includes a first stopper configured to fix the first power transmitter; and a second stopper configured to fix the ring gear.

In some example embodiments, the second power transmitter has an elliptical shape, and the plurality of power transmitters include a flexspline configured to be elastically deformed in response to a rotation of the second power transmitter; and a circular spline configured to enclose the flexspline, the circular spline having a toothed shape configured to engage with at least a portion of an outer circumferential surface of the flexspline.

Some example embodiments relate to a motion assistance apparatus.

In some example embodiments, the motion assistance apparatus includes an actuator and a driving frame. The actuator including, a plurality of power transmitters configured to transmit power sequentially, the plurality of power transmitters including a first power transmitter and a second power transmitter, the first power transmitter and the second power transmitter being adjacent ones of the plurality of power transmitters and configured to perform coaxial rotation motion, an elastic element configured to connect the first power transmitter and the second power transmitter, and a motor configured to transmit the power to an input end of the plurality of power transmitters. The driving frame configured to receive the power from an output end of the plurality of power transmitters and transmit the power to a user.

In some example embodiments, the actuator includes a first angle sensor configured to measure a first rotation angle of the first power transmitter; a second angle sensor configured to measure a second rotation angle of the second power transmitter; and a controller configured to determine a torque to be applied between the motor and the driving frame based on the first rotation angle and the second rotation angle.

In some example embodiments, the first angle sensor is connected to the motor such that the first rotation angle measured thereby is a rotation angle of a drive shaft of the motor, and the second angle sensor is connected to the driving frame such that the second rotation angle measured thereby is a rotation angle of the driving frame.

In some example embodiments, the plurality of power transmitters include a first planetary gear set and a second planetary gear set, the first planetary gear set including a carrier and first planetary gears, the carrier configured to receive power from the first planetary gears, and the second planetary gear set including a sun gear and second planetary gears, the sun gear configured to transmit the power to the second planetary gears, and the controller is configured to determine the first rotation angle and the second rotation angle based on gear ratios for the carrier and the sun gear, respectively, and determine the torque to apply to the elastic element based on a difference between the first rotation angle and the second rotation angle, and an elasticity coefficient of the elastic element.

In some example embodiments, the controller is configured to determine the torque such that the torque counteracts a deformation of the elastic element.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
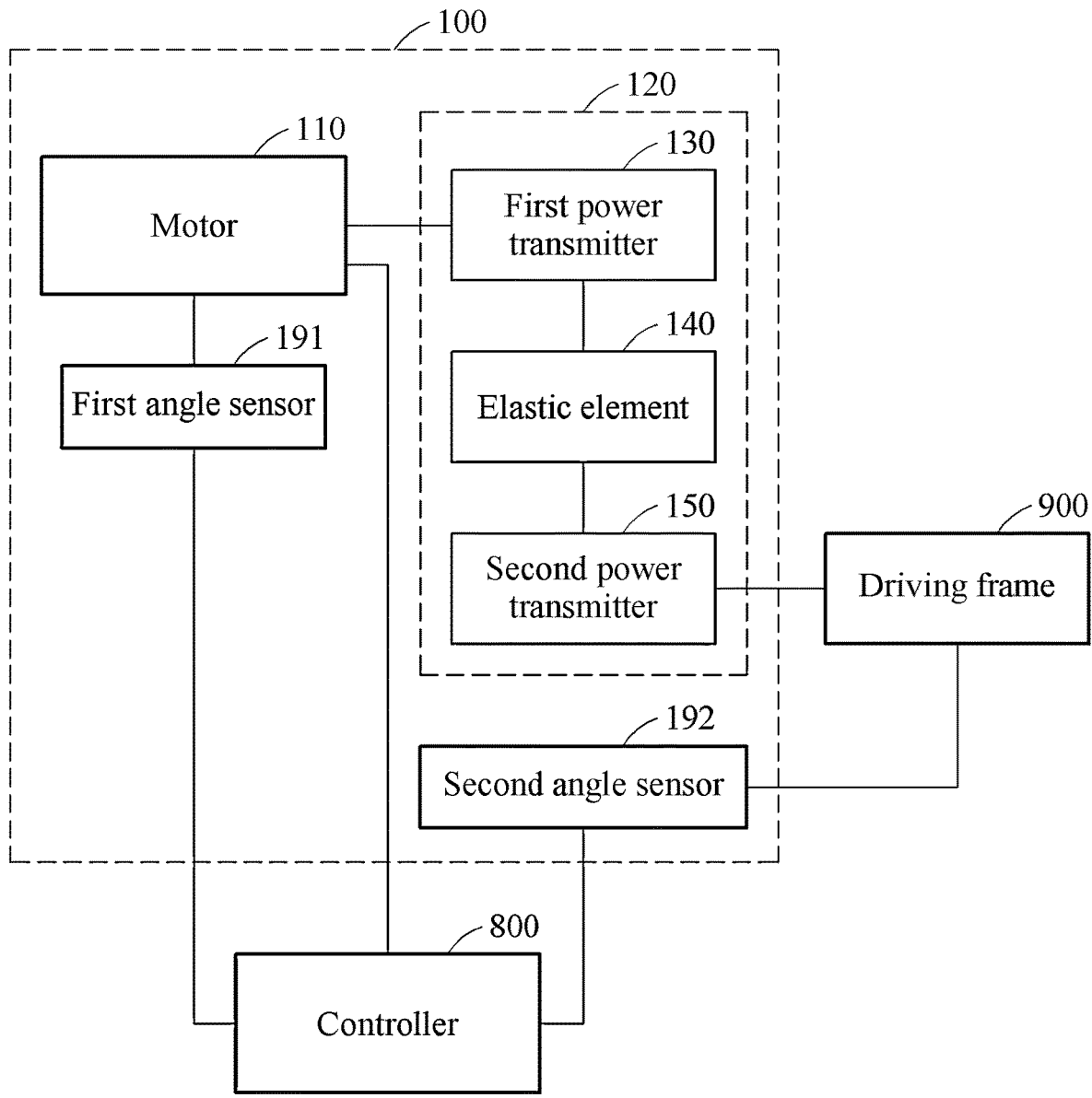
FIG. 1 is a block diagram illustrating an actuator and a driving frame according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

FIG. 1 is a block diagram illustrating an actuator and a driving frame according to at least one example embodiment.

Referring to FIG. 1, an actuator 100 may drive a driving frame 900.

The driving frame 900 may be applied to a robot or an industrial facility. For example, the driving frame 900 may be a power transmitting member of a motion assistance apparatus that supports one or more sides of a body of a user and assist a motion of a joint of the user. The actuator 100 may include a motor 110, a reducer 120, a first angle sensor 191, and a second angle sensor 192.

The motor 110 may generate power to be transmitted to the driving frame 900. The power generated by the motor 110 may be reduced while passing through the reducer 120 and transmitted to the driving frame 900. An output end of the motor 110 may be connected to an input end of the reducer 120.

The reducer 120 may reduce the power generated by the motor 110 and transmit the reduced power to the driving frame 900. The reducer 120 may include a plurality of power transmitters configured to transmit the power sequentially. For example, the reducer 120 may include a first power transmitter 130, an elastic element 140, and a second power transmitter 150 that are connected in series.

The first power transmitter 130 may rotate using the power received from the motor 110. The first power transmitter 130 may be the input end of the reducer 120 that is connected directly to the output end of the motor 110, or a power transmitter that receives the power from the input end of the reducer 120. That is, another power transmitter may be connected between the first power transmitter 130 and the motor 110.

The second power transmitter 150 may receive the power from the first power transmitter 130, and transmit the power to the driving frame 900. The second power transmitter 150 may be an output end of the reducer 120, or a power transmitter that transmits the power to the output end of the reducer 120. That is, another power transmitter may be connected between the second power transmitter 150 and the driving frame 900.

The first power transmitter 130 and the second power transmitter 150 may perform a coaxial rotation motion. That is, the first power transmitter 130 and the second power transmitter 150 may have the same rotation axis.

The elastic element 140 may connect the first power transmitter 130 and the second power transmitter 150 in series. The first power transmitter 130 and the second power transmitter 150 may be adjacent to each other and perform a coaxial rotation motion. In a case in which an external force is not applied to the driving frame 900, the whole power generated by the motor 110 may be transmitted from the first power transmitter 130 to the second power transmitter 150. Conversely, when an external force is applied to the driving frame 900, a portion of the power generated by the motor 110 may be used to deform the elastic element 140, and a remaining portion thereof may be transmitted to the second power transmitter 150. For example, in a case in which the driving frame 900 is a frame of the motion assistance apparatus, the external force applied to the driving frame 900 may be an interaction torque between the driving frame 900 and the user. When the interaction torque increases, a torque to deform the elastic element 140 may also increase.

The first angle sensor 191 may measure a rotation angle of the first power transmitter 130. The first angle sensor 191 may be connected to one side of the first power transmitter 130 and directly measure the rotation angle of the first power transmitter 130. In another example, the first angle sensor 191 may indirectly measure the rotation angle of the first power transmitter 130 based on a gear ratio from the motor 110 to the first power transmitter 130, by measuring a rotation angle of a drive shaft of the motor 110. The first angle sensor 191 may transmit information related to the measured rotation angle of the first power transmitter 130 to a controller 800.

The second angle sensor 192 may measure a rotation angle of the second power transmitter 150. The second angle sensor 192 may be connected to one side of the second power transmitter 150 and directly measure the rotation angle of the second power transmitter 150. In another example, the second angle sensor 192 may be connected to one side of the driving frame 900, and indirectly measure the rotation angle of the second power transmitter 150 based on a gear ratio from the second power transmitter 150 to the driving frame 900. The second angle sensor 192 may transmit information related to the measured rotation angle of the second power transmitter 150 to the controller 800.

The controller 800 may include a memory and processing circuitry (not shown).

The memory (not shown) may include at least one of a volatile memory, non-volatile memory, random access memory (RAM), a flash memory, a hard disk drive, and an optical disk drive.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in the memory (not shown), as a special purpose computer to determine a torque to be applied between the first power transmitter 130 and the second power transmitter 150 based on the rotation angles measured by the first angle sensor 191 and the second angle sensor 192. Further, the processing circuitry may be configured to sense a gait phase of a user, and drive a stopper module based on results of the same to change a gear ratio.

Therefore, the processing circuitry may improve the functioning of the actuator 100 itself by measuring an interaction force through the elastic element 140 without using separate force/torque sensors and a force amplifier, thus, reducing a size of the actuator while allowing the elastic element 140 to absorb impact to improve the durability of the actuator.

The elastic element 240 may be deformed by a torque applied between the first carrier 233 and the second sun gear 251. The elastic element 240 may absorb an impact applied to the driving frame 900, thereby improving a durability of the actuator 200.

For example, the controller 800 may determine the torque based on a difference between the rotation angles of the first power transmitter 130 and the second power transmitter 150, and an elasticity coefficient of the elastic element 140. The controller 800 may be physically separate from the actuator 100, or may be a part of the actuator 100 if a space suffices.

In a case in which the elastic element 140 has a constant elasticity coefficient irrespective of a deformation angle, the controller 800 may determine the difference between the rotation angles of the first power transmitter 130 and the second power transmitter 150 to be the deformation angle of the elastic element 140, and determine the torque to be applied between the first power transmitter 130 and the second power transmitter 150 by multiplying the deformation angle by the elasticity coefficient of the elastic element 140. That is, when AO denotes the difference between the rotation angles of the first power transmitter 130 and the second power transmitter 150, and k denotes the elasticity coefficient of the elastic element 140, the controller 800 may determine the interaction torque T using Equation 1.

$$T=k\Delta\theta \quad \text{[Equation 1]}$$

Meanwhile, the controller 800 may pre-store torque information with respect to a deformation angle of the elastic element 140 measured through an experiment or a computation. The controller 800 may determine the interaction torque T with respect to the deformation angle based on the torque information. In this example, although the elasticity coefficient of the elastic element 140 changes non-linearly based on the deformation angle, the interaction torque T may be determined.

The controller 800 may control a magnitude of the power to be transmitted from the actuator 100 to the driving frame 900 based on the interaction torque T.

Figure 2:
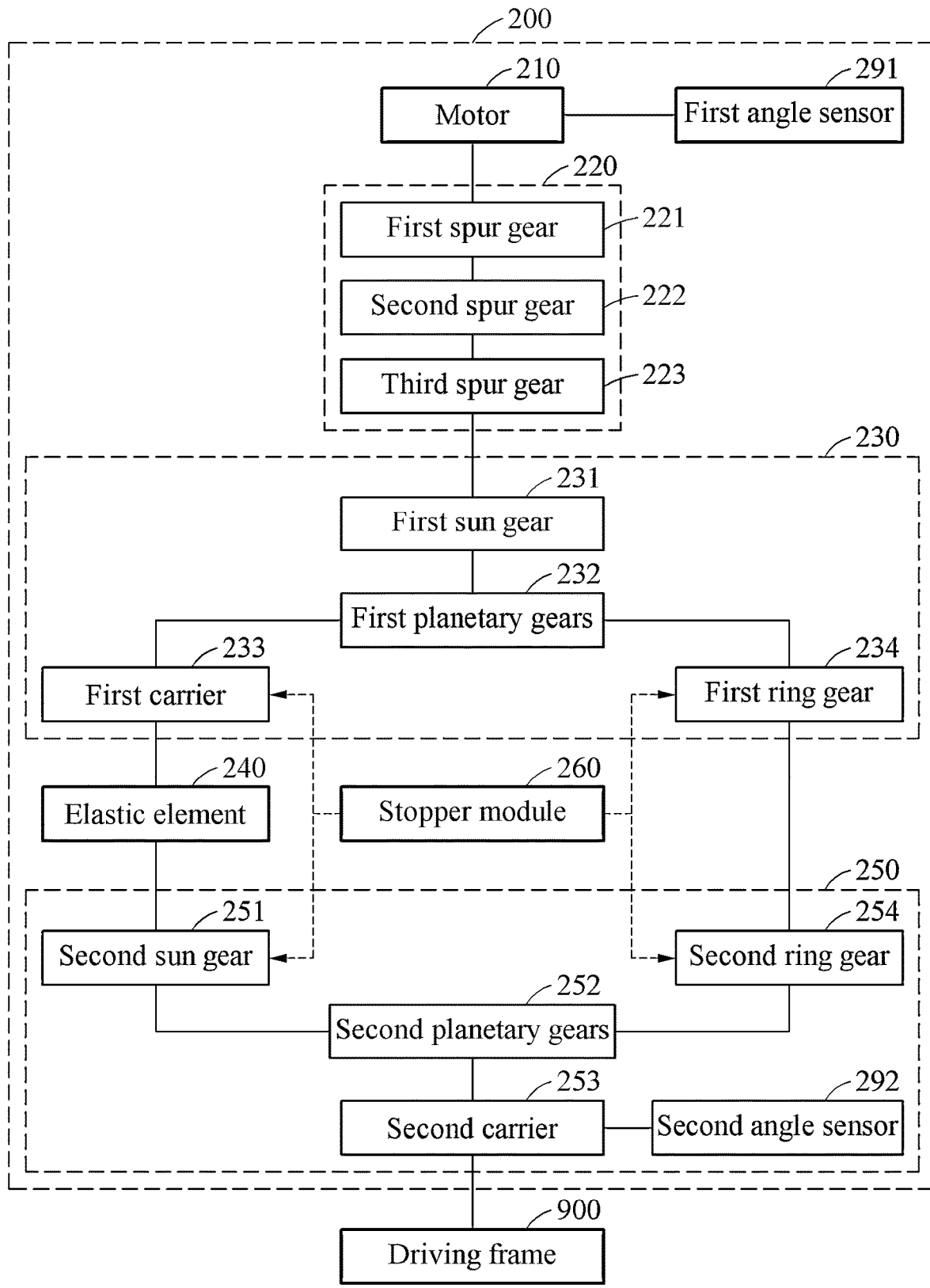
FIG. 2 is a block diagram illustrating an actuator and a driving frame according to at least one example embodiment.
Figure 3:
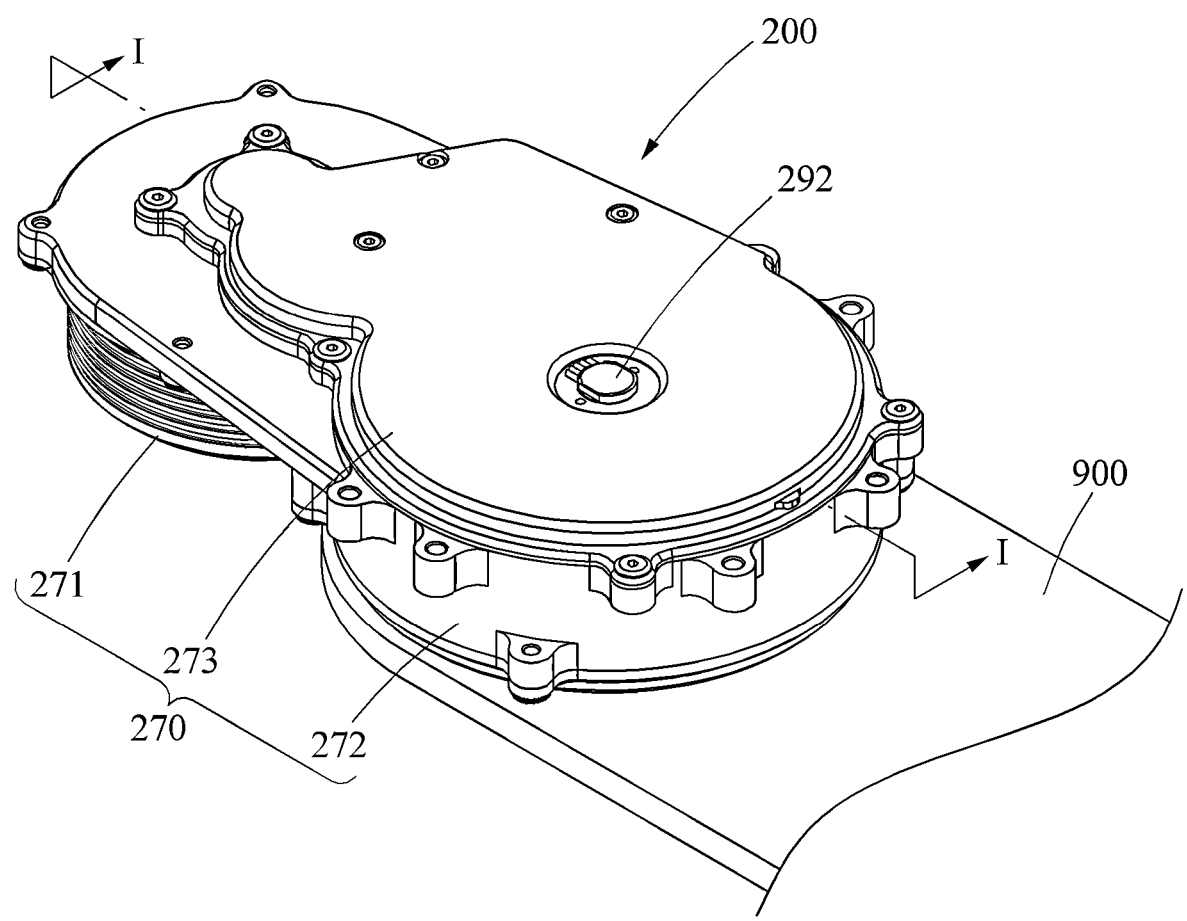
FIG. 3 is a perspective view illustrating an actuator and a driving frame according to at least one example embodiment.
Figure 4:
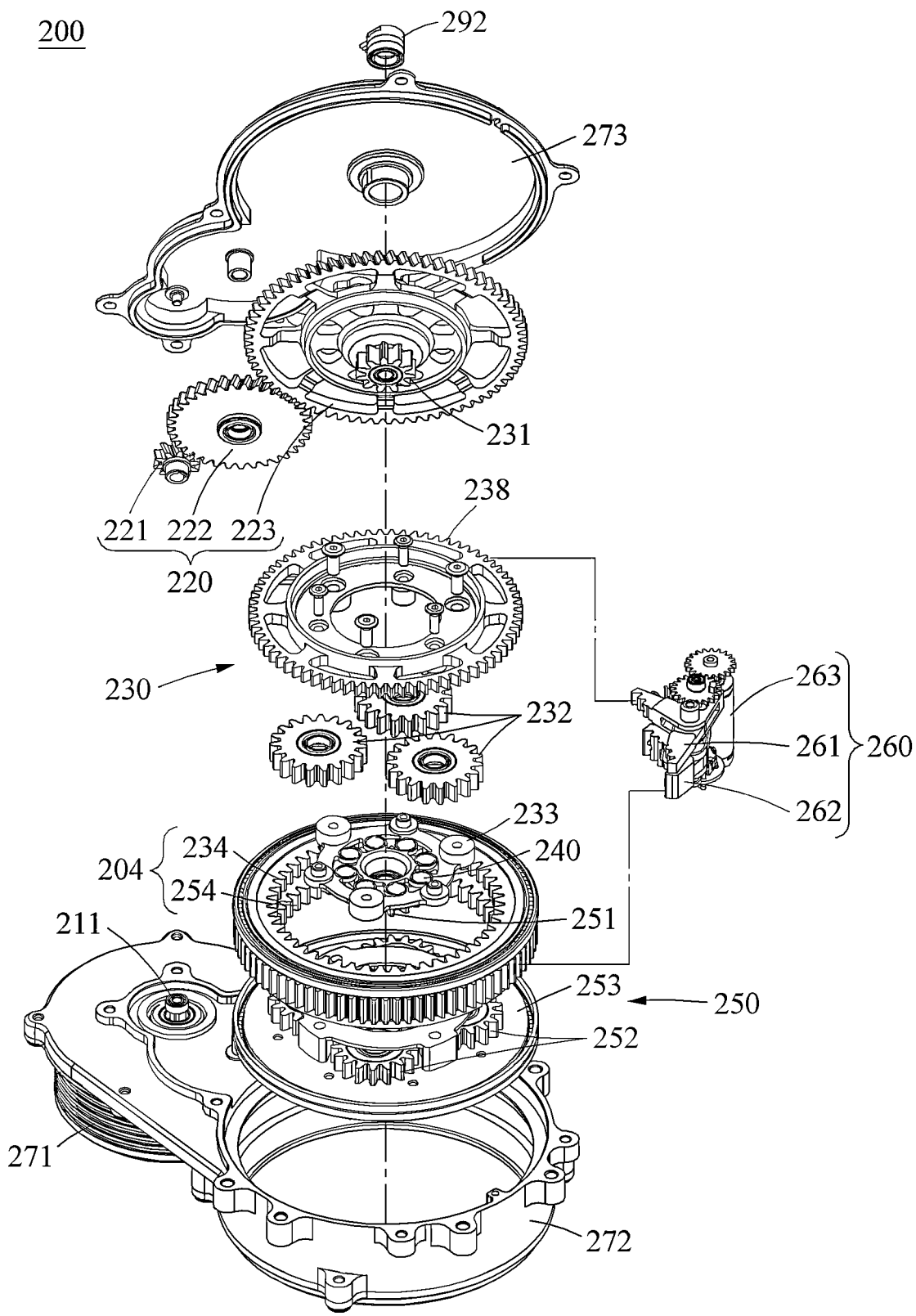
FIG. 4 is an exploded perspective view illustrating an actuator according to at least one example embodiment.
Figure 5:
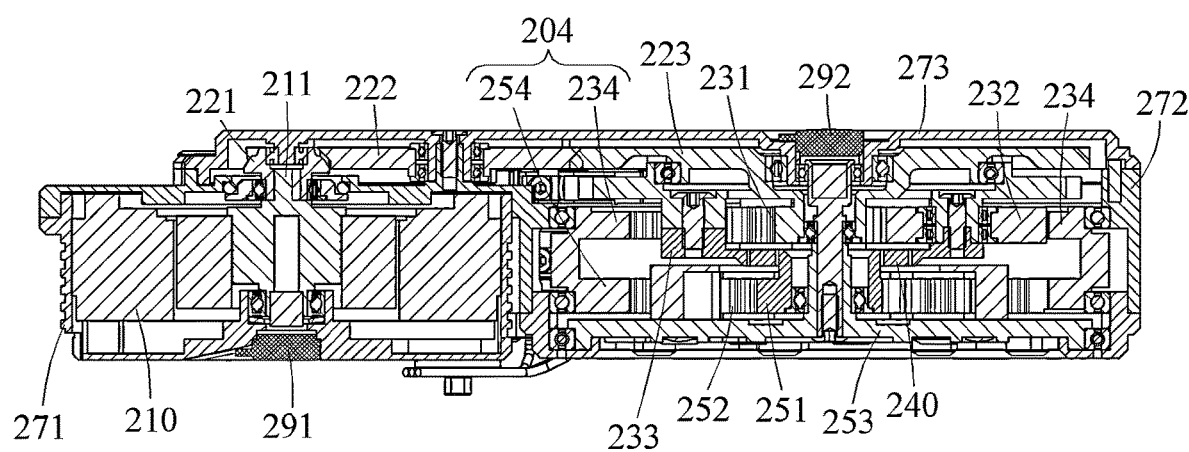
FIG. 5 is a cross-sectional view illustrating the actuator of FIG. 3, cut along a line I-I.

FIG. 2 is a block diagram illustrating an actuator and a driving frame according to at least one example embodiment, FIG. 3 is a perspective view of the actuator, FIG. 4 is an exploded perspective view of the actuator, and FIG. 5 is a cross-sectional view of the actuator, cut along a line I-I of FIG. 3.

Referring to FIGS. 2 through 5, an actuator 200 may include a motor 210, a gear train 220, a first planetary gear set 230, an elastic element 240, a second planetary gear set 250, a stopper module 260, a case 270, a first angle sensor 291, and a second angle sensor 292. The actuator 200 may be connected to the driving frame 900. A controller is omitted from FIGS. 2 through 5 to simplify the drawings.

A first power transmitter and a second power transmitter may be power transmitters that are adjacent to each other and perform a coaxial rotation motion, among a plurality of power transmitters constituting the gear train 220, the first planetary gear set 230, and the second planetary gear set 250. For example, the first power transmitter may correspond to a first carrier 233 of the first planetary gear set 230, and the second power transmitter may be a second sun gear 251 of the second planetary gear set 250 (refer to FIGS. 2 and 4). In another example, the first power transmitter may be a spur gear 223 which is an output end of the gear train 220, and the second power transmitter may be a first sun gear 231 which is an input end of the first planetary gear set 230. For ease of description, FIGS. 2 through 5 will be described based on a case in which the first power transmitter is the first carrier 233, and the second power transmitter is the second sun gear 251. Herein, the first power transmitter 233 and the first carrier 233 may be interchangeably used, and the second power transmitter 251 and the second sun gear 251 may be interchangeably used.

The gear train 220 may include a plurality of spur gears 221, 222, and 223. The plurality of spur gears may include a first spur gear 221, a second spur gear 222, and a third spur gear 223 that are connected in series. Although FIGS. 2 through 5 illustrate three spur gears constituting the gear train 220, the number of the spur gears is not limited thereto.

The first spur gear 221 may be detachably connected to a drive shaft 211 of the motor 210. The first spur gear 221 may be rotated by the drive shaft 211 of the motor 210.

The second spur gear 222 may engage with one side of the first spur gear 221. A diameter of the second spur gear 222 may be greater than a diameter of the first spur gear 221, and the number of teeth of the second spur gear 222 may be greater than the number of teeth of the first spur gear 221. Thus, power may be reduced while being transmitted from the first spur gear 221 to the second spur gear 222.

The third spur gear 223 may engage with one side of the second spur gear 222. A diameter of the third spur gear 223 may be greater than the diameter of the second spur gear 222, and the number of teeth of the third spur gear 223 may be greater than the number of the teeth of the second spur gear 222. Thus, power may be reduced while being transmitted from the second spur gear 222 to the third spur gear 223.

The first planetary gear set 230 may receive power from the gear train 220, reduce the received power, and transmit the reduced power to the second planetary gear set 250. The first planetary gear set 230 may include the first sun gear 231, first planetary gears 232, the first carrier 233, a first ring gear 234, and a rotary plate 238.

The first sun gear 231 may be connected to one side of the third spur gear 223. The first sun gear 231 and the third spur gear 223 may perform a coaxial rotation motion.

The first planetary gears 232 may engage with the first sun gear 231 and the first ring gear 234 at the same time. For example, the first planetary gears 232 may engage with an outer circumferential surface of the first sun gear 231, and engage with an inner circumferential surface of the first ring gear 234. The first planetary gears 232 may rotate or revolve using the power received from the first sun gear 231. In this example, the first planetary gears 232 may revolve around a rotation center of the first sun gear 231. For a stable operation of the first planetary gear set 230, the first planetary gears 232 may be radially spaced equal angles apart from each other about the rotation center of the first sun gear 231. FIG. 4 illustrates a total of three first planetary gears 232 spaced apart at intervals of 120 degrees.

The first carrier 233 may be connected to rotation axes of the first planetary gears 232, and rotate about the rotation center of the first sun gear 231. The first carrier 233 may rotate at a revolution velocity of the first planetary gears 232. That is, the first carrier 233 may rotate when the first planetary gears 232 revolve. For example, the first carrier 233 may be ring-shaped.

The rotary plate 238 may fix the rotation axes of the first planetary gears 232. The first planetary gears 232 may be between the rotary plate 238 and the first carrier 233. The rotary plate 238 may perform a coaxial rotation motion with the first carrier 233. The rotary plate 238 may include a hole at a center thereof such that the first sun gear 231 may pass through the hole. The rotary plate 238 may include, on an outer circumferential surface thereof, external teeth that engage with a first stopper 261 of the stopper module 260.

The first ring gear 234 may be a ring-shaped gear that encloses outer sides of the first planetary gears 232, and may have an inner circumferential surface with internal teeth that engage with teeth on outer circumferential surfaces of the first planetary gears 232. In addition to the internal teeth, the first ring gear 234 may also include external teeth that engage with a second stopper 262 of the stopper module 260.

One of the first carrier 233 and the first ring gear 234 may selectively function as a power output end of the first planetary gear set 230.

The second planetary gear set 250 may receive the power from the first planetary gear set 230, reduce the received power, and transmit the reduced power to the driving frame 900. The second planetary gear set 250 may include the second sun gear 251, second planetary gears 252, a second carrier 253, and a second ring gear 254.

The second sun gear 251 may receive the power from the first carrier 233 of the first planetary gear set 230 and transmit the power to the second planetary gears 252. The second sun gear 251 may be at a revolution center of the second planetary gears 252.

Similar to the second sun gear 251, the second ring gear 254 may function as one of a plurality of power input ends of the second planetary gear set 250. The second ring gear 254 may receive the power from the first ring gear 234 and transmit the power to the second planetary gears 252. The second ring gear 254 may include internal teeth that engage with the second planetary gears 252, and external teeth that engage with the second stopper 262 of the stopper module 260. As shown in FIG. 4, the first ring gear 234 and the second ring gear 254 may be provided as an integral body. For example, the first ring gear 234 and the second ring gear 254 may form an upper portion and a lower portion of an integrated ring gear 204, respectively. In this example, the first ring gear 234 and the second ring gear 254 may have the same rotation velocity.

The second planetary gears 252 may be between the second sun gear 251 and the second ring gear 254 and engage with both the second sun gear 251 and the second ring gear 254. The second planetary gears 252 may rotate or revolve using the power received from the second sun gear 251 or the second ring gear 254. In this example, the second planetary gears 252 may revolve around a rotation center of the second sun gear 251.

The second carrier 253 may be connected to rotation axes of the second planetary gears 252, and rotate about the rotation center of the second sun gear 251. The second carrier 253 may rotate at a revolution velocity of the second planetary gears 252. As described above, the second carrier 253 may function as a power output end of the second planetary gear set 250, thereby transmitting the power to the driving frame 900.

The elastic element 240 may connect the first carrier 233, for example, the first power transmitter, and the second sun gear 251, for example, the second power transmitter. The elastic element 240 may be deformed by an external force applied to the driving frame 900. The elastic element 240 may be deformed by a torque applied between the first carrier 233 and the second sun gear 251. The elastic element 240 may absorb an impact applied to the driving frame 900, thereby improving a durability of the actuator 200.

The stopper module 260 may include the first stopper 261 configured to fix the rotary plate 238, the second stopper 262 configured to fix the integrated ring gear 204, and a stopper motor 263 configured to drive the first stopper 261 and the second stopper 262.

When the first stopper 261 engages with the external teeth of the rotary plate 238, rotations of the first carrier 233 and the second sun gear 251 may be restrained, and the power may be transmitted sequentially through the first sun gear 231, the first planetary gears 232, the first ring gear 234, the second ring gear 254, the second planetary gears 252, and the second carrier 253 to the driving frame 900.

When the second stopper 262 engages with the external teeth of the integrated ring gear 204, rotations of the first ring gear 234 and the second ring gear 254 may be restrained, and the power may be transmitted sequentially through the first sun gear 231, the first planetary gears 232, the first carrier 233, the elastic element 240, the second sun gear 251, the second planetary gears 252, and the second carrier 253 to the driving frame 900.

The stopper motor 263 may connect one of the first stopper 261 and the second stopper 262 to a corresponding power transmitter, and disconnect the other stopper from a corresponding power transmitter. For example, the stopper motor 263 may fix the first stopper 261 to engage with the external teeth of the rotary plate 238, and separate the second stopper 262 from the integrated ring gear 204, thereby implementing a low reduction mode. In another example, the stopper motor 263 may separate the first stopper 261 from the rotary plate 238, and fix the second stopper 262 to engage with the external teeth of the integrated ring gear 204, thereby implementing a high reduction mode. That is, the stopper module 260 may selectively fix one of the first power transmitter 233, for example, the first carrier 233, and the integrated ring gear 204, thereby changing a gear ratio from the first sun gear 231 to the second carrier 253.

The stopper motor 263 may be electrically connected to a sensor (not shown) configured to sense a gait phase of a user, thereby driving the first stopper 261 and the second stopper 262. For example, at a level walking stage of the user, the stopper motor 263 may fix the first stopper 261 to engage with the external teeth of the rotary plate 238, thereby implementing the low reduction mode. In another example, when the user stands up, the stopper motor 263 may fix the second stopper 262 to engage with the external teeth of the integrated ring gear 204, thereby implementing the high reduction mode.

The case 270 may receive the plurality of power transmitters. The case 270 may protect the plurality of power transmitters from an external impact. The case 270 may include a motor receiver 271, a main receiver 272, and a cover 273.

The motor receiver 271 may receive the motor 210. The motor 210 may include a ring-shaped stator, and a rotor configured to rotate in an inner wall of the stator, and the motor receiver 271 may have a cylindrical shape with an internal hollow to receive the motor 210.

The main receiver 272 may receive the plurality of power transmitters. The main receiver 272 may have a cylindrical shape with an internal hollow, and the first planetary gear set 230, the elastic element 240, the second planetary gear set 250, and the stopper module 260 may be in the internal hollow of the main receiver 272.

The cover 273 may be detachably coupled to one side of one of the motor receiver 271 and the main receiver 272. The cover 273 may close openings of the motor receiver 271 and the main receiver 272, thereby preventing an invasion of water into the actuator 200. The cover 273 may be coupled to each of the motor receiver 271 and the main receiver 272 through a plurality of coupling devices, for example, bolts and nuts. The user may separate the cover 273, and easily replace the plurality of power transmitters and the elastic element 240.

The motor receiver 271 may overlap at least a portion of the main receiver 272 in a direction perpendicular to the drive shaft 211 of the motor 210. The internal hollows of the motor receiver 271 and the main receiver 272 may be parallel to each other. In this example, the motor 210 with a relatively great height may be parallel to the plurality of power transmitters, for example, the first planetary gear set 230, the elastic element 240, and the second planetary gear set 250, such that a total height of the actuator 200 may be reduced and thus, a protruding height thereof from the user may be reduced.

The first angle sensor 291 may be connected to the motor 210, and measure a rotation angle of the drive shaft 211 of the motor 210. The second angle sensor 292 may be connected to the second carrier 253 which is the output end of the plurality of power transmitters, and measure a rotation angle of the second carrier 253. The controller (not shown) may determine a torque to be applied to the elastic element 240 based on the rotation angles measured by the first angle sensor 291 and the second angle sensor 292.

The controller may determine rotation angles for the first carrier 233 and the second sun gear 251 based on gear ratios among the power transmitters, and determine the torque to be applied to the elastic element 240 by multiplying a difference between the rotation angles by an elasticity coefficient of the elastic element 240.

The driving frame 900 may be a frame configured to assist a motion of a body part of the user. For example, the driving frame 900 may be attached to one side of a thigh of the user, and assist a flexion motion and an extension motion of a hip joint of the user. However, a connection position of the driving frame 900 is not limited thereto.

Figure 6:
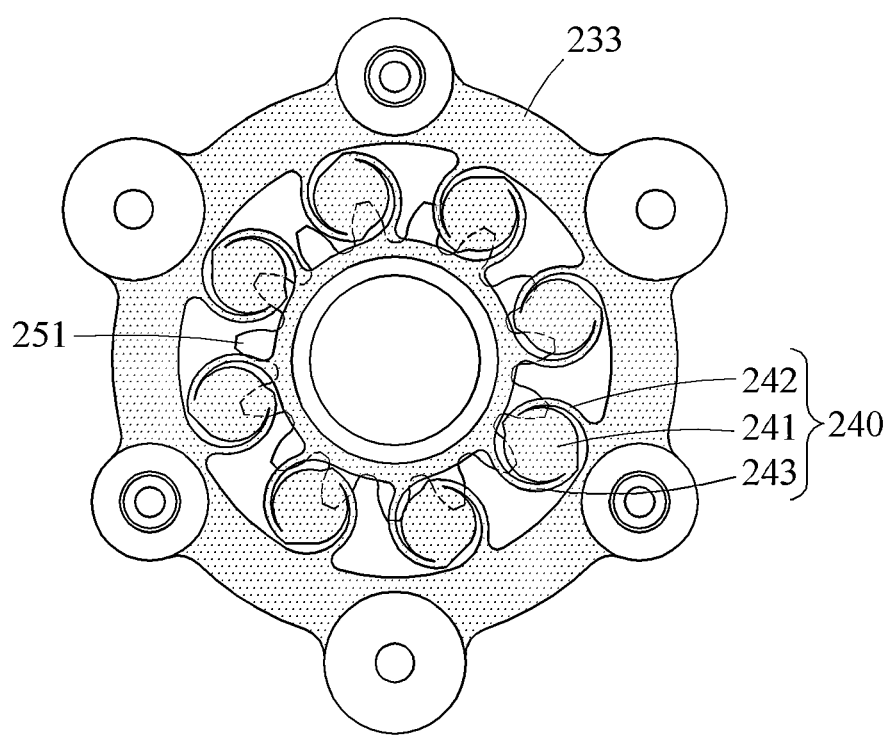
FIG. 6 is a plan view illustrating a first power transmitter, a second power transmitter, and an elastic element, the elastic element yet to be elastically deformed, according to at least one example embodiment.
Figure 7:
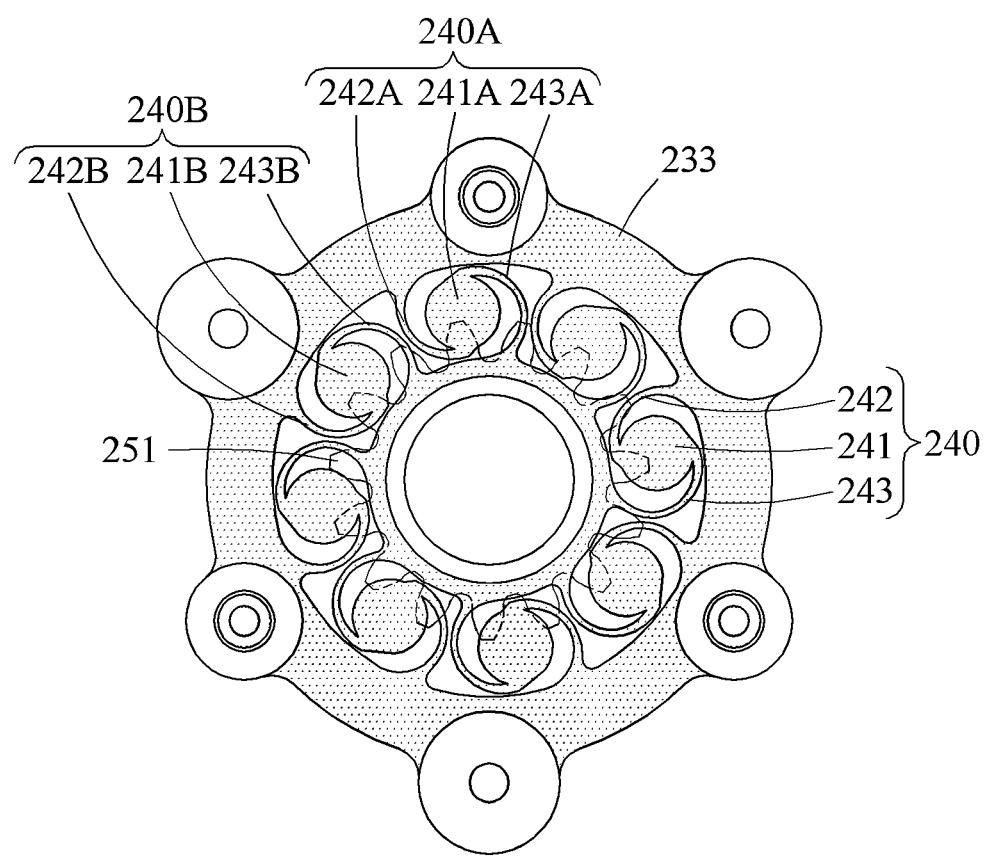
FIG. 7 is a plan view illustrating a first power transmitter, a second power transmitter, and an elastic element, the elastic element elastically deformed, according to at least one example embodiment.
Figure 8:
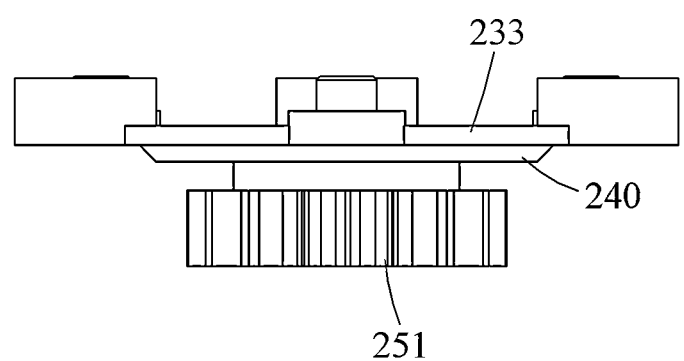
FIG. 8 is a front view illustrating a first power transmitter, a second power transmitter, and an elastic element according to at least one example embodiment.

FIG. 6 is a plan view illustrating a first power transmitter, a second power transmitter, and an elastic element, the elastic element yet to be elastically deformed, according to at least one example embodiment. FIG. 7 is a plan view illustrating a first power transmitter, a second power transmitter, and an elastic element, the elastic element elastically deformed, according to at least one example embodiment. FIG. 8 is a front view illustrating a first power transmitter, a second power transmitter, and an elastic element according to at least one example embodiment.

Referring to FIGS. 6 and 7, the first power transmitter 233, the second power transmitter 251, and the elastic element 240 may be provided as an integral body. The first power transmitter 233 and the second power transmitter 251 may perform a coaxial rotation motion. The elastic element 240 may be deformed by a difference between rotation angles of the first power transmitter 233 and the second power transmitter 251.

The first power transmitter 233 may be ring-shaped. The first power transmitter 233 may include holes radially spaced equal angles apart from each other. The holes may fix rotation axes of the plurality of first planetary gears 232.

The elastic element 240 may be between an inner wall of the first power transmitter 233 and an outer wall of the second power transmitter 251. The above structure may reduce the height of the actuator 200. The elastic element 240 may include a body 241, a first connector 242, and a second connector 243.

Bodies 241 may be radially spaced equal angles apart from each other along the inner wall of the first power transmitter 233. Referring to FIGS. 6 and 7, eight bodies 241 may be at intervals of 45 degrees along the inner wall of the first power transmitter 233. However, the number of the bodies 241 is not limited thereto.

A first end of the first connector 242 may be fixed to the inner wall of the first power transmitter 233, and a second end of the first connector 242 may be fixed to a portion of the body 241 relatively close to the outer wall of the second power transmitter 251 from a center of the body 241. For example, the first connector 242 may have a curved shape that encloses a first portion of the body 241. When the first power transmitter 233 and the second power transmitter 251 relatively rotate, a distance between the first connector 242 and the body 241 may increase or decrease. In the example of FIGS. 6 and 7, when the first power transmitter 233 rotates counterclockwise, the second power transmitter 251 may rotate an angle less than a rotation angle of the first power transmitter 233 due to an interaction force, and thus the distance between the first connector 242 and the body 241 may increase.

A first end of the second connector 243 may be fixed to the outer wall of the second power transmitter 251, and a second end of the second connector 243 may be fixed to a portion of the body 241 relatively close to the inner wall of the first power transmitter 233 from the center of the body 241. For example, the second connector 243 may have a curved shape that encloses a second portion of the body 241. The first portion and the second portion of the body 241 may be on opposite sides from the center of the body 241. When the first power transmitter 233 and the second power transmitter 251 relatively rotate, a distance between the second connector 243 and the body 241 may increase or decrease. In the example of FIGS. 6 and 7, when the first power transmitter 233 rotates counterclockwise, the second power transmitter 251 may rotate an angle less than a rotation angle of the first power transmitter 233 due to an interaction force, and the distance between the second connector 243 and the body 241 may increase.

A plurality of elastic elements 240 may be spaced apart from each other at equal intervals about a rotation axis of the first power transmitter 233 and the second power transmitter 251 due to the interaction force. The above structure may limit a range of a relative rotation angle between the first power transmitter 233 and the second power transmitter 251.

When the first power transmitter 233 and the second power transmitter 251 relatively rotate a set angle, two adjacent elastic elements of the plurality of elastic elements 240, for example, elastic elements 240A and 240B, may be in contact with each other. In detail, a first connector 242A of one elastic element 240A of the two adjacent elastic elements 240A and 240B may be in contact with a second connector 243B of the other one elastic element 240B, whereby the relative rotation angle of the first power transmitter 233 and the second power transmitter 251 may be limited. For example, in a case of an elderly person having a joint problem, a relatively great number of elastic elements 240 may be used to set a relatively low upper limit of the relative rotation angle, thereby reducing excessive increase in a range of a working angle of a joint.

When the motor 210 is driven in a reverse direction, the first power transmitter 233 may rotate clockwise, and the second power transmitter 251 may rotate clockwise an angle less than the rotation angle of the first power transmitter 233 due to the interaction force. In this example, the distance between the body 241 and the first connector 242, and the distance between the body 241 and the second connector 243 may decrease. When the interaction force is greater than or equal to a set magnitude, the body 241 may be in contact with the first connector 242 or the second connector 243. That is, the body 241, the first connector 242, and the second connector 243 may limit the relative rotation angle between the first power transmitter 233 and the second power transmitter 251. The body 241 may have a circular shape so as to be in surface contact with the first connector 242 and the second connector 243 having curved shapes FIG. 9 is a front view illustrating a first power transmitter, a second power transmitter, and an elastic element according to at least one example embodiment.

Figure 9:
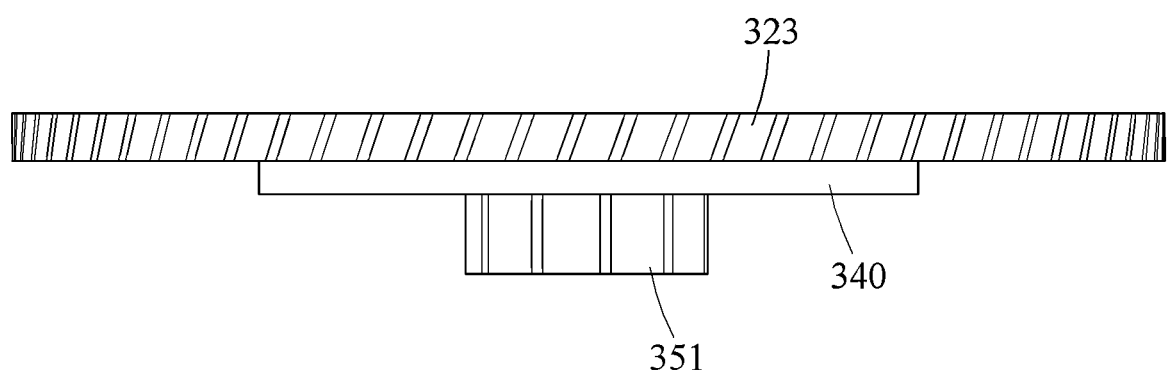
FIG. 9 is a front view illustrating a first power transmitter, a second power transmitter, and an elastic element according to at least one example embodiment.

Referring to FIG. 9, an elastic element 340 may be between a spur gear 323 which is an output end of a gear train and a sun gear 351 which is an input end of a planetary gear set. A first angle sensor may directly or indirectly measure a rotation angle of the spur gear 323, and a second angle sensor may directly or indirectly measure a rotation angle of the sun gear 351. A controller may determine a deformation angle of the elastic element 340 based on the rotation angles measured by the first angle sensor and the second angle sensor, and determine an interaction force between an actuator and an outside thereof based on the deformation angle.

Figure 10:
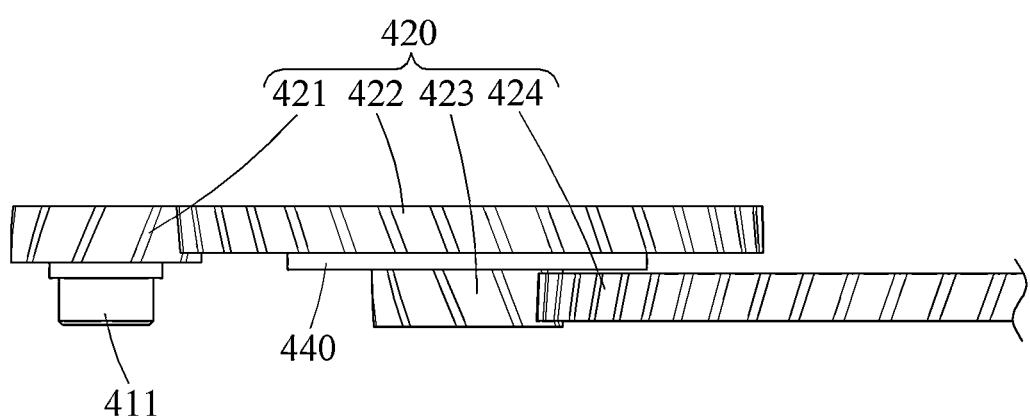
FIG. 10 is a front view illustrating a drive shaft of a motor, a plurality of power transmitters, and an elastic element according to at least one example embodiment.

FIG. 10 is a front view illustrating a drive shaft of a motor, a plurality of power transmitters, and an elastic element according to at least one example embodiment.

Referring to FIG. 10, an elastic element 440 may be in a gear train 420 including a plurality of spur gears. For example, the gear train 420 may include a first spur gear 421 connected to a drive shaft 411 of a motor to receive power, a second spur gear 422 configured to rotate while engaging with the first spur gear 421, a third spur gear 423 configured to perform a coaxial rotation motion with the second spur gear 422, and a fourth spur gear 424 configured to rotate while engaging with the third spur gear 423.

The elastic element 440 may be between the second spur gear 422 and the third spur gear 423 that perform the coaxial rotation motion. A first angle sensor may directly or indirectly measure a rotation angle of the second spur gear 422, and a second angle sensor may directly or indirectly measure a rotation angle of the third spur gear 423. A controller may determine a deformation angle of the elastic element 440 based on the rotation angles measured by the first angle sensor and the second angle sensor, and determine an interaction force between an actuator and an outside thereof based on the deformation angle.

Figure 11:
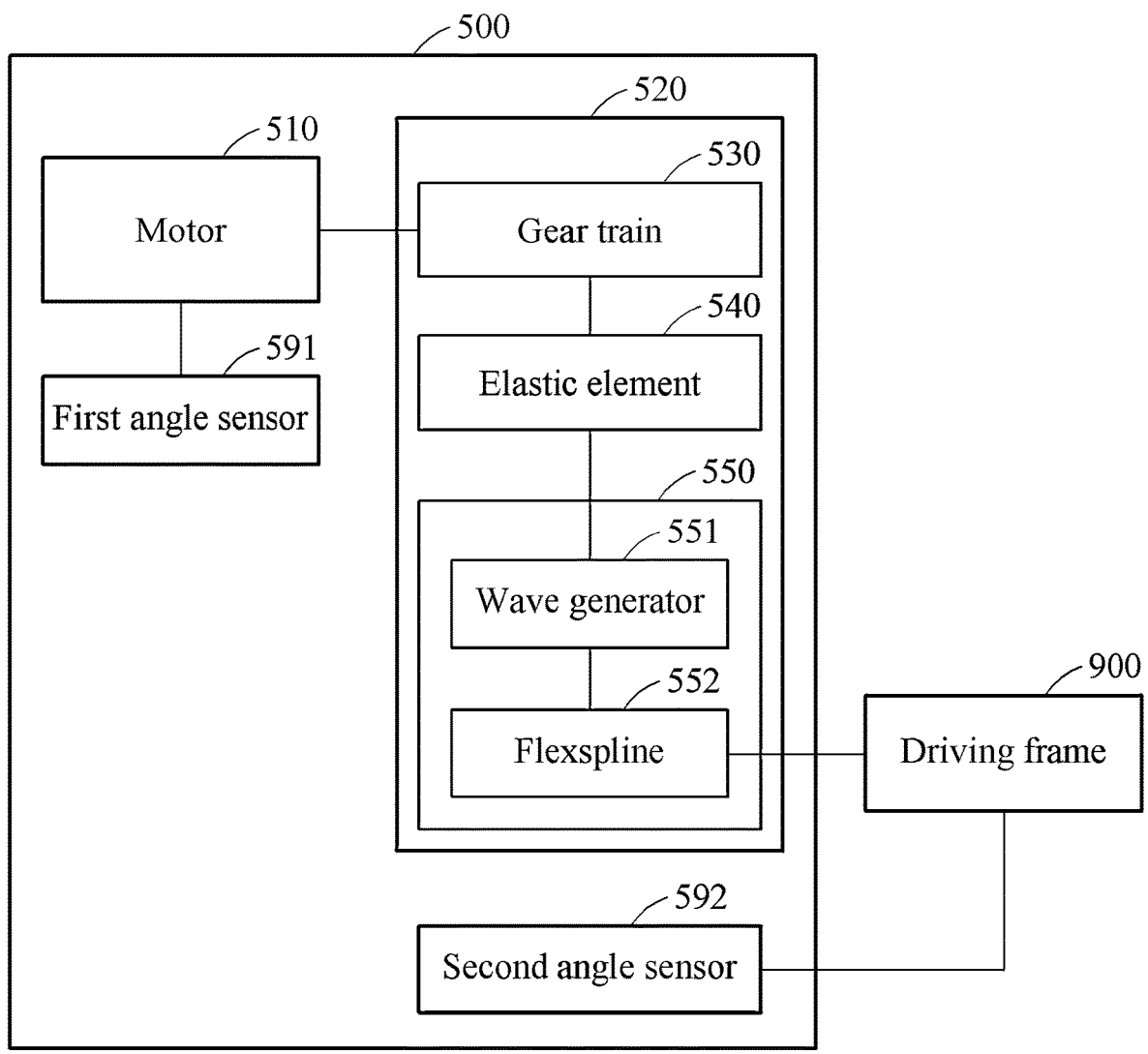
FIG. 11 is a block diagram illustrating an actuator and a driving frame according to at least one example embodiment.
Figure 12:
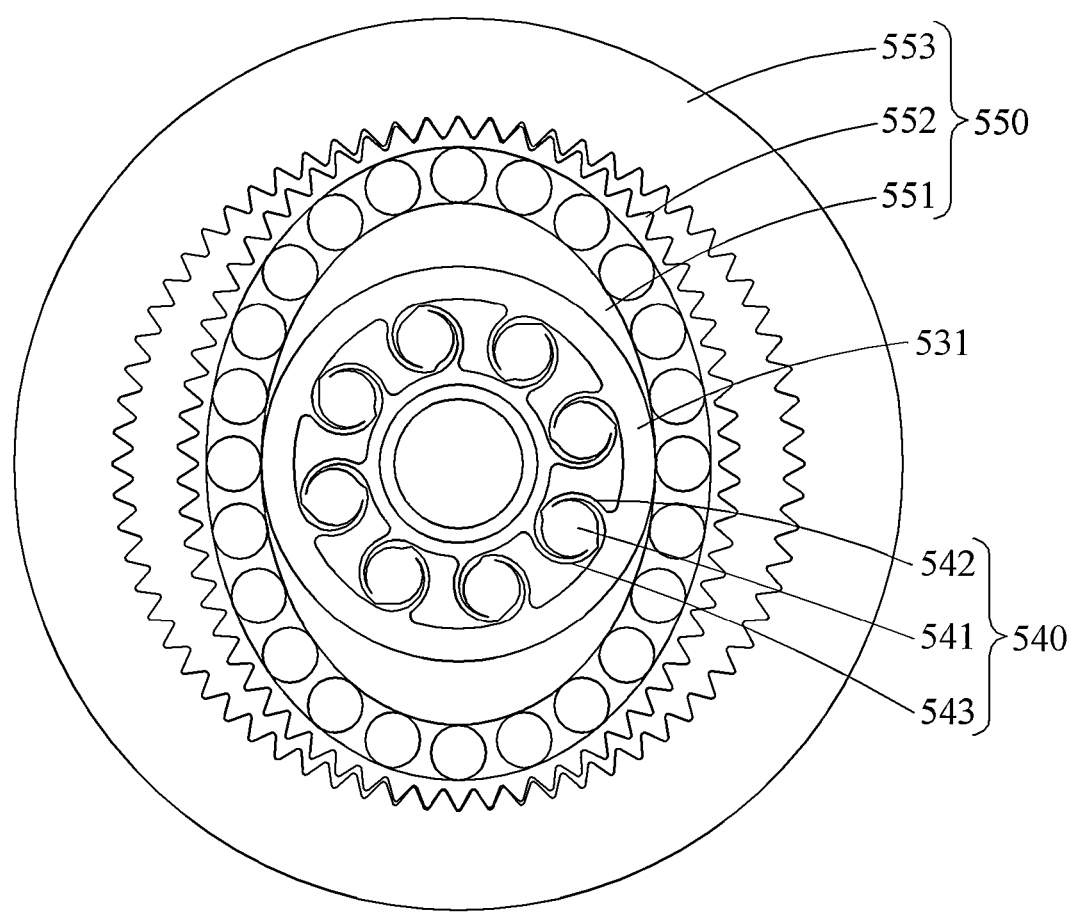
FIG. 12 is a plan view illustrating a first power transmitter, a second power transmitter, an elastic element, a flexspline, and a circular spline, the elastic element yet to be elastically deformed, according to at least one example embodiment.
Figure 13:
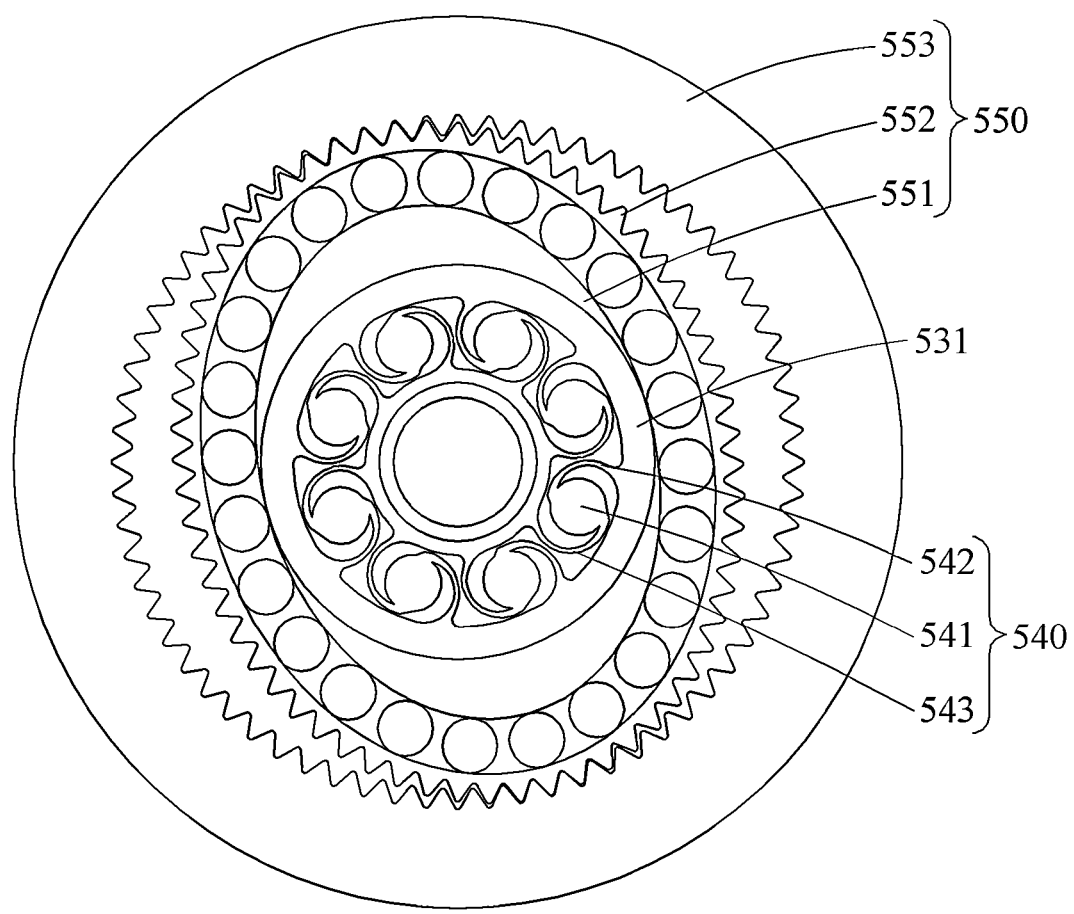
FIG. 13 is a plan view illustrating a first power transmitter, a second power transmitter, an elastic element, a flexspline, and a circular spline, the elastic element elastically deformed, according to at least one example embodiment.

FIG. 11 is a block diagram illustrating an actuator and a driving frame according to at least one example embodiment. FIG. 12 is a plan view illustrating a first power transmitter, a second power transmitter, an elastic element, a flexspline, and a circular spline, the elastic element yet to be elastically deformed, according to at least one example embodiment. FIG. 13 is a plan view illustrating a first power transmitter, a second power transmitter, an elastic element, a flexspline, and a circular spline, the elastic element elastically deformed, according to at least one example embodiment.

Referring to FIGS. 11 through 13, an actuator 500 may include a motor 510, a reducer 520, a first angle sensor 591, and a second angle sensor 592. The reducer 520 may include a gear train 530 configured to transmit power in series, an elastic element 540, and a harmonic drive 550. The harmonic drive 550 may include a wave generator 551, a flexspline 552, and a circular spline 553.

The wave generator 551 may have an elliptical shape. A plurality of ball bearings may be on an outer circumferential surface of the wave generator 551. The wave generator 551 may rotate using power received from the elastic element 540. The wave generator 551 may be an input end of the harmonic drive 550.

The flexspline 552 may be a metal elastic body. The flexspline 552 may be elastically deformed in response to a rotation of the wave generator 551 having the elliptical shape. The flexspline 552 may be an output end of the harmonic drive 550. The flexspline 552 may include external teeth on an outer circumferential surface thereof.

The circular spline 553 may be ring-shaped. The circular spline 553 may include internal teeth on an inner circumferential surface thereof, the internal teeth engaging with the external teeth of the flexspline 552. The number of the internal teeth of the circular spline 553 may be greater than the number of the external teeth of the flexspline 552. Both ends of a major axis of the flexspline 552 may engage with the inner circumferential surface of the circular spline 553, and both ends of a minor axis of the flexspline 552 may be spaced apart from the inner circumferential surface of the circular spline 553.

The elastic element 540 may include a body 541, a first connector 542, and a second connector 543. The elastic element 540 may be between a spur gear 531 which is an output end of the gear train 530 and the wave generator 551 which is an input end of the harmonic drive 550, the spur gear 531 and the wave generator 551 performing a coaxial rotation motion. The elastic element 540 may be deformed by an interaction force between the actuator 500 and the driving frame 900.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An actuator, comprising:
a plurality of power transmitters configured to transmit power sequentially, the plurality of power transmitters including a first power transmitter and a second power transmitter, the first power transmitter and the second power transmitter being adjacent ones of the plurality of power transmitters and configured to perform coaxial rotation motion;
an elastic element configured to connect the first power transmitter and the second power transmitter, the elastic element having a body, a first connector extending in a first direction from a first end of the body, and a second connector extending in a second direction from second end of the body, the second direction being opposite the first direction such that the first connector, the body, and the second connector form an s-shape with an end of the first connector being fixed to an inner wall of the first power transmitter and an end of the second connector being fixed to an outer wall of the second power transmitter, the elastic element configured to configured to deform a deformation amount in response to an external force applied to the second power transmitter such that the deformation amount corresponds to a magnitude of the external force applied to a driving frame;
a first angle sensor configured to measure a first rotation angle of the first power transmitter; and
a second angle sensor configured to measure a second rotation angle of the second power transmitter.

2. The actuator of claim 1, further comprising:
a controller configured to determine a torque to apply based on a difference between the first rotation angle and the second rotation angle.

3. The actuator of claim 1, further comprising:
a motor configured to transmit the power to the plurality of power transmitters; and
a case including a motor receiver and a main receiver such that the motor receiver overlaps at least a portion of the main receiver in a direction perpendicular to a drive shaft of the motor, the motor receiver configured to receive the motor, and the main receiver configured to receive the first power transmitter, the second power transmitter, and the elastic element.

4. The actuator of claim 3, wherein the case further includes a cover detachably coupled to one side of each of the motor receiver and the main receiver.

5. The actuator of claim 1, wherein
the first power transmitter is ring-shaped, and
the elastic element is between the inner wall of the first power transmitter and the outer wall of the second power transmitter.

6. The actuator of claim 5, wherein the first power transmitter, the elastic element, and the second power transmitter are an integral body.

7. The actuator of claim 5, wherein
the body has a circular shape,
the first connector has a curved shape that encloses a first portion of the body, and
the second connector has a curved shape that encloses a second portion of the body.

8. The actuator of claim 5, wherein the elastic element includes a plurality of elastic elements spaced apart from each other at equal intervals about a rotation axis shared by the first power transmitter and the second power transmitter.

9. The actuator of claim 8, wherein two adjacent elastic elements of the plurality of elastic elements are in contact with each other when the first power transmitter and the second power transmitter rotate relative to one another by a set angle.

10. The actuator of claim 1, wherein the plurality of power transmitters comprise:
a first planetary gear having a rotation axis rotatably fixed to the first power transmitter, the first planetary gear configured to revolve around a rotation axis of the first power transmitter;
a first sun gear configured to transmit the power to the first planetary gear;
a second planetary gear configured to engage with an outer circumferential surface of the second power transmitter, and revolve around a rotation axis of the second power transmitter;
a carrier to which the second planetary gear is rotatably installed, the carrier configured to perform the coaxial rotation motion with the second power transmitter; and
a ring gear configured to engage with the first planetary gear and the second planetary gear.

11. The actuator of claim 10, further comprising: a motor configured to generate the power to drive the plurality of power transmitters,
wherein
the plurality of power transmitters further include a gear train configured to connect the motor and the first sun gear.

12. The actuator of claim 11, wherein the gear train has a first side and a second side, and the motor, the first power transmitter, the second power transmitter, and the elastic element are on a same one of the first side and the second side of the gear train.

13. The actuator of claim 10, further comprising:
at least one stopper configured to change a gear ratio between the first sun gear and the carrier by selectively fixing one of the first power transmitter and the ring gear.

14. The actuator of claim 13, wherein the at least one stopper comprises:
a first stopper configured to fix the first power transmitter; and
a second stopper configured to fix the ring gear.

15. The actuator of claim 1, wherein the second power transmitter has an elliptical shape, and the plurality of power transmitters comprise:

a flexspline configured to be elastically deformed in response to a rotation of the second power transmitter; and
a circular spline configured to enclose the flexspline, the circular spline having a toothed shape configured to engage with at least a portion of an outer circumferential surface of the flexspline.

16. A motion assistance apparatus, comprising:
an actuator including,
a plurality of power transmitters configured to transmit power sequentially, the plurality of power transmitters including a first power transmitter and a second power transmitter, the first power transmitter and the second power transmitter being adjacent ones of the plurality of power transmitters and configured to perform coaxial rotation motion,
an elastic element configured to connect the first power transmitter and the second power transmitter, the elastic element having a body, a first connector extending in a first direction from a first end of the body, and a second connector extending in a second direction from second end of the body, the second direction being opposite the first direction such that the first connector, the body, and the second connector form an s-shape with an end of the first connector being fixed to an inner wall of the first power transmitter and an end of the second connector being fixed to an outer wall of the second power transmitter, the elastic element configured to configured to deform a deformation amount in response to an external force applied to the second power transmitter such that the deformation amount corresponds to a magnitude of the external force applied to a driving frame,
a motor configured to transmit the power to an input end of the plurality of power transmitters,
a first angle sensor configured to measure a first rotation angle of the first power transmitter, and
a second angle sensor configured to measure a second rotation angle of the second power transmitter; and
the driving frame configured to receive the power from an output end of the plurality of power transmitters and transmit the power to a user.

17. The motion assistance apparatus of claim 16, wherein
the first angle sensor is connected to the motor such that the first rotation angle measured thereby is a rotation angle of a drive shaft of the motor, and
the second angle sensor is connected to the driving frame such that the second rotation angle measured thereby is a rotation angle of the driving frame.

18. The motion assistance apparatus of claim 16, wherein the plurality of power transmitters include a first planetary gear set and a second planetary gear set, the first planetary gear set including a carrier and first planetary gears, the carrier configured to receive power from the first planetary gears, and the second planetary gear set including a sun gear and second planetary gears, the sun gear configured to transmit the power to the second planetary gears.

19. The motion assistance apparatus of claim 18, further comprising:
a controller configured to determine a torque to apply such that the torque counteracts the deformation amount of the elastic element.

\* \* \* \* \*